US012590937B2

(12) United States Patent
Jo et al.

(10) Patent No.: US 12,590,937 B2
(45) Date of Patent: Mar. 31, 2026

(54) METHOD AND APPARATUS FOR CALIBRATING CTD OBSERVATION INFORMATION

(71) Applicant: National Institute of Meteorological Sciences, Seogwipo-si (KR)

(72) Inventors: Hyeong Jun Jo, Jeju-si (KR); Sungho Choo, Seogwipo-si (KR); Kiryong Kang, Seogwipo-si (KR); Chulkyu Lee, Seoul (KR); Kyungsuck Ko, Mokpo-si (KR)

(73) Assignee: NATIONAL INSTITUTE OF METEOROLOGICAL SCIENCES, Seogwipo-si (KR)

( * ) Notice: Subject to any disclaimer, the term of this patent is extended or adjusted under 35 U.S.C. 154(b) by 460 days.

(21) Appl. No.: 18/319,424

(22) Filed: May 17, 2023

(65) Prior Publication Data

US 2024/0183834 A1     Jun. 6, 2024

(30) Foreign Application Priority Data

Dec. 1, 2022    (KR) ........................ 10-2022-0165940

(51) Int. Cl.
*G01N 33/18*            (2006.01)
(52) U.S. Cl.
CPC .................................... *G01N 33/18* (2013.01)
(58) Field of Classification Search
CPC ...................................................... G01N 33/18
See application file for complete search history.

(56) References Cited

U.S. PATENT DOCUMENTS

| 12,106,521 | B2 * | 10/2024 | Varekamp | ............ H04N 13/246 |
| 2020/0005543 | A1 * | 1/2020 | Kim | ...................... G06T 19/006 |
| 2021/0005020 | A1 * | 1/2021 | Özbek | ................ G02B 27/0093 |

FOREIGN PATENT DOCUMENTS

| JP | 4998039 B2 * | 8/2012 | ............. G01N 27/07 |
| KR | 102437532 | 8/2022 | |

OTHER PUBLICATIONS

Martini et al., Corrections for Pumped SBE 41CP CTDs Determined from Stratified Tank Experiments, Journal of Atmospheric and Oceanic Technology, Apr. 2019, vol. 36, pp. 733-744 (Year: 2019).*
Martini et al., Corrections for Pumped SBE 41CP CTDs Determined from Stratified Tank Experiments, Journal of Atmospheric and Oceanic Technology, Apr. 2019, vol. 36, pp. 733-744.
Min et al., Quality Control of Observed Temperature Time Series from the Korea Ocean Research Stations: Preliminary Application of Ocean Observation Initiative's Approach and Its Limitation, Ocean and Polar Research, Sep. 2020, vol. 42, No. 3, pp. 195-210.

* cited by examiner

*Primary Examiner* — Lee E Rodak
*Assistant Examiner* — Zannatul Ferdous
(74) *Attorney, Agent, or Firm* — CANTOR COLBURN LLP

(57)            ABSTRACT

Provided is a conductivity temperature depth (CTD) observation information calibrating method and the CTD observation information calibrating method incudes receiving CTD observation raw information; calibrating the CTD observation raw information; and outputting calibrated CTD observation information.

14 Claims, 6 Drawing Sheets

| | |
|---|---|
| FIRST DIGIT OF FLAG INFORMATION: | DETERMINE SPIKE FOR WATER TEMPERATURE INFORMATION (0: NO SPIKE/1: SUSPECTED SPIKE) |
| SECOND DIGIT OF FLAG INFORMATION: | DETERMINE CONSECUTIVE SAME VALUE FOR WATER TEMPERATURE INFORMATION (0: NO CONSECUTIVE SAME VALUE/1: SUSPECTED CONSECUTIVE SAME VALUE) |
| THIRD DIGIT OF FLAG INFORMATION: | DETERMINE CLIMATIC VALUE FOR WATER TEMPERATURE INFORMATION (A IS WATER TEMPERATURE INFORMATION) (0: $-\sigma \leq A \leq \sigma$ / 1: $\sigma < A \leq 2\sigma$ / 2: $2\sigma < A \leq 3\sigma$ / 3: $3\sigma < A$) (9: $-2\sigma \leq A < -\sigma$ / 8: $-3\sigma \leq A < -2\sigma$ / 7: $A < -3\sigma$) |
| FOURTH DIGIT OF FLAG INFORMATION: | DETERMINE SPIKE FOR SALINITY INFORMATION (0: NO SPIKE/1: SUSPECTED SPIKE) |
| FIFTH DIGIT OF FLAG INFORMATION: | DETERMINE CONSECUTIVE SAME VALUE FOR FOR SALINITY INFORMATION (0: NO CONSECUTIVE SAME VALUE/1: SUSPECTED CONSECUTIVE SAME VALUE) |
| SIXTH DIGIT OF FLAG INFORMATION: | DETERMINE CLIMATIC VALUE FOR SALINITY INFORMATION (A IS SALINITY INFORMATION) (0: $-\sigma \leq A \leq \sigma$ / 1: $\sigma < A \leq 2\sigma$ / 2: $2\sigma < A \leq 3\sigma$ / 3: $3\sigma < A$) (9: $-2\sigma \leq A < -\sigma$ / 8: $-3\sigma \leq A < -2\sigma$ / 7: $A < -3\sigma$) |
| SEVENTH DIGIT OF FLAG INFORMATION: | DETERMINE DENSITY INVERSION (0: NO DENSITY INVERSION/1: DENSITY INVERSION) |

FIG. 5

| 124.4167 | 32.5000 | 5.0000 | 99.0000 | 99.0000 | 99.0000 | 0000000 |
| 124.4167 | 32.5000 | 6.0000 | 99.0000 | 99.0000 | 99.0000 | 0000000 |
| 124.4167 | 32.5000 | 7.0000 | 27.5930 | 26.0467 | 1015.8386 | 0020070 |
| 124.4167 | 32.5000 | 8.0000 | 27.5676 | 26.1138 | 1015.9012 | 0020070 |
| 124.4167 | 32.5000 | 9.0000 | 27.3135 | 26.1555 | 1016.0161 | 0010070 |
| 124.4167 | 32.5000 | 10.0000 | 25.0943 | 26.9340 | 1017.2762 | 0010070 |
| 124.4167 | 32.5000 | 11.0000 | 22.0863 | 27.9603 | 1018.9050 | 0000070 |
| 124.4167 | 32.5000 | 12.0000 | 21.4305 | 28.2102 | 1019.2744 | 0000070 |
| 124.4167 | 32.5000 | 13.0000 | 21.2083 | 28.3256 | 1019.4252 | 0000070 |
| 124.4167 | 32.5000 | 14.0000 | 20.1885 | 28.9887 | 1020.1981 | 0000070 |
| 124.4167 | 32.5000 | 15.0000 | 18.6791 | 29.7083 | 1021.1279 | 0000080 |
| 124.4167 | 32.5000 | 16.0000 | 18.1374 | 29.9837 | 1021.4735 | 0000080 |
| 124.4167 | 32.5000 | 17.0000 | 17.7153 | 30.2211 | 1021.7598 | 0000080 |
| 124.4167 | 32.5000 | 18.0000 | 17.1258 | 30.3937 | 1022.0341 | 0000080 |
| 124.4167 | 32.5000 | 19.0000 | 15.7725 | 30.8799 | 1022.7165 | 0090080 |
| 124.4167 | 32.5000 | 20.0000 | 15.4273 | 31.0172 | 1022.9017 | 0090080 |
| 124.4167 | 32.5000 | 21.0000 | 15.3018 | 31.0615 | 1022.9675 | 0090080 |
| 124.4167 | 32.5000 | 22.0000 | 15.2529 | 31.0729 | 1022.9911 | 0090080 |
| 124.4167 | 32.5000 | 23.0000 | 15.2305 | 31.0764 | 1023.0033 | 0090080 | a

METHOD AND APPARATUS FOR CALIBRATING CTD OBSERVATION INFORMATION

BACKGROUND

Field

The present disclosure relates to a method and an apparatus for calibrating conductivity temperature depth (CTD) observation information.

Description of the Related Art

A weather ship "Gisang 1" operated by Korean Meteorological Administration actively performs regular and special observation using a conductivity temperature depth (CTD) recorder. A CTD recorder of the related art is equipment which vertically observes the water temperature and salinity 24 times per second and measures from the vicinity of a surface layer to a water depth approximately 3 to 5 m higher than a seabed at an observation point.

However, raw data produced through the CTD observation includes a large number of abnormal data due to the influence such as whether a pump operates, an observation frequency, and lifting/lowering of the equipment so that a quality of observation data is degraded.

A background art of the present disclosure is disclosed in Korean Registered Patent Publication No. 10-2437532.

SUMMARY

The present disclosure has made an effort to solve the problems of the related art and an object thereof is to provide a CTD observation information calibrating method and apparatus which solve the problem of degradation of a quality of CTD observation data.

However, objects to be achieved by various embodiments of the present disclosure are not limited to the technical objects as described above and other technical objects may be present.

As a technical means to achieve the above-described technical object, according to an aspect of the present disclosure, a conductivity temperature depth (CTD) observation information calibrating method includes receiving CTD observation raw information; calibrating the CTD observation raw information; and outputting calibrated CTD observation information.

According to an exemplary embodiment of the present disclosure, in the calibrating, pump flag information is written in the CTD observation raw information based on a pump state.

According to an exemplary embodiment of the present disclosure, in the calibrating, first valid information is derived from the CTD observation raw information based on the pump flag information.

According to an exemplary embodiment of the present disclosure, the calibrating includes: generating second valid information by attenuating noise from the first valid information.

According to an exemplary embodiment of the present disclosure, in the generating of second valid information, the second valid information is generated based on a predetermined median part of predetermined information for every water depth included in the first valid information.

According to an exemplary embodiment of the present disclosure, in the calibrating, after determining whether water temperature information and salinity information included in the second valid information are present within a predetermined threshold water temperature range and a predetermined threshold salinity range, a predetermined missing value is inserted into the water temperature information present out of the threshold water temperature range and the salinity information present out of the threshold salinity range to generate third valid information.

According to an exemplary embodiment of the present disclosure, in the calibrating, the missing value is inserted into information having a difference from information for every water depth adjacent by a predetermined degree which is equal to or larger than a predetermined degree in the third valid information and spike flag information is written to generate fourth valid information.

According to an exemplary embodiment of the present disclosure, in the calibrating, consecutive same value flag information is written in the fourth valid information based on the sameness of the information in the predetermined unit water depth range to generate fifth valid information.

According to an exemplary embodiment of the present disclosure, in the calibrating, climatic value flag information is written in information present out of a predetermined threshold climatic value range of the fifth valid information to generate sixth valid information.

According to an exemplary embodiment of the present disclosure, in the calibrating, density inversion flag information is written in the sixth valid information based on density difference from an upper water depth in a predetermined range to generate the calibrated CTD observation information.

According to an exemplary embodiment of the present disclosure, in the calibrating, when a specific value does not satisfy a condition, the specific value is replaced with a predetermined missing value.

According to an exemplary embodiment of the present disclosure, in the calibrating, flag information is written in the CTD observation raw information for every water depth.

According to an exemplary embodiment of the present disclosure, in the outputting, flag information corresponding to the calibrated CTD observation information is output.

According to an aspect of the present disclosure, a conductivity temperature depth (CTD) observation information calibrating apparatus includes a receiving unit configured to receive CTD observation raw information; a calibrating unit configured to calibrate the CTD observation raw information; and an output unit configured to output calibrated CTD observation information.

The above-described solving means are merely illustrative but should not be construed as limiting the present disclosure. In addition to the above-described embodiments, additional embodiments may be further provided in the drawings and the detailed description of the present disclosure.

According to the objects of the present disclosure, the CTD observation information calibrating method and apparatus are provided to solve the problem of degradation of the quality of the CTD observation data.

However, the effect which can be achieved by the present disclosure is not limited to the above-described effects, there may be other effects.

BRIEF DESCRIPTION OF THE DRAWINGS

The above and other aspects, features and other advantages of the present disclosure will be more clearly understood from the following detailed description taken in conjunction with the accompanying drawings, in which:

FIG. 4 is a view illustrating an example of a flag information setting screen according to an exemplary embodiment of the present disclosure;

FIG. 5 is a view illustrating a flag information output screen according to an exemplary embodiment of the present disclosure;

DETAILED DESCRIPTION OF THE EMBODIMENT

Figure 1:
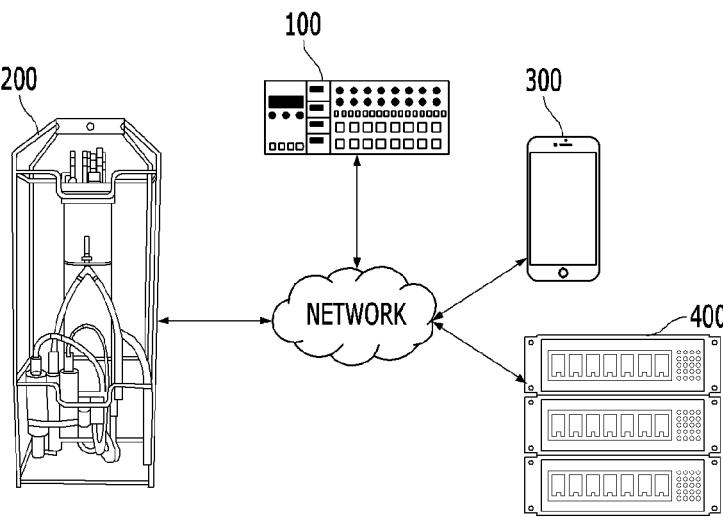
FIG. 1 is a schematic diagram of a CTD observation information calibrating system according to an exemplary embodiment of the present disclosure.

Hereinafter, the present disclosure will be described more fully with reference to the accompanying drawings, in which exemplary embodiments of the present disclosure are shown. However, the present disclosure can be realized in various different forms, and is not limited to the embodiments described herein. Accordingly, in order to clearly explain the present disclosure in the drawings, portions not related to the description are omitted. Like reference numerals designate like elements throughout the specification.

Throughout this specification and the claims that follow, when it is described that an element is "coupled" to another element, the element may be "directly coupled" to the other element or "electrically coupled" or "indirectly coupled" to the other element through a third element.

Through the specification of the present disclosure, when one member is located "on", "above", "on an upper portion", "below", "under", and "on a lower portion" of the other member, the member may be adjacent to the other member or a third member may be disposed between the above two members.

In the specification of the present disclosure, unless explicitly described to the contrary, the word "comprise" and variations such as "comprises" or "comprising", will be understood to imply the inclusion of stated elements but not the exclusion of any other elements.

FIG. 1 is a schematic diagram of a CTD observation information calibrating system according to an exemplary embodiment of the present disclosure.

Referring to FIG. 1, a conductivity temperature depth (CTD) observation information calibrating system 10 (hereinafter, referred to as "the present system 10") includes a CTD observation information calibrating apparatus 100 (hereinafter, referred to as "the present apparatus 100"), a CTD device 200, a user terminal 300, and an external server 400, but is not limited thereto.

For example, in the present system 10, the present apparatus 100 may receive CTD observation raw information from the CTD device 200, calibrate the received CTD observation raw information, and output the calibrated CTD observation information.

According to the exemplary embodiment of the present disclosure, the present apparatus 100 may provide a CTD observation raw information reception menu, a CTD observation raw information calibration menu, and a CTD observation raw information output menu. For example, the user terminal 300 downloads and installs an application program provided by the present apparatus 100, and the CTD observation raw information reception menu, the CTD observation raw information calibration menu, and the CTD observation raw information output menu may be provided through the installed application.

The present apparatus 100 may include all kinds of servers, terminals, or devices having functions of transmitting and receiving data, contents, and various communication signals with the CTD device 200, the user terminal 300, and the external server 400 via a network and storing and processing data.

The CTD device 200 may interwork with the present apparatus 100, the user terminal 300, and the external server 400 and measure a water temperature, the salinity, a water depth, an electrical conductivity, dissolved oxygen, pH (hydrogen ion concentration), and the like of the seawater. The CTD device 200 may be operated in the weather ship and perform regular and special observation. A CTD device 200 of the related art is a device which vertically observes the water temperature and salinity 24 times per second and measure from the vicinity of a surface layer to a water depth approximately 3 to 5 m higher than a seabed at an observation point.

The user terminal 300 is a device which interworks with the present apparatus 100, the CTD device 200, and the external server 400 via the network, and for example, may be all kinds of wireless communication devices such as a smart phone, a smart pad, a tablet PC, a wearable device, a personal communication system (PCS), a global system for mobile communication (GSM), a personal digital cellular (PDC), a personal handyphone system (PHS), a personal digital assistant (PDA), an international mobile telecommunication (IMT)-2000, code division multiple access (CDMA)-2000, W-code division multiple access (W-CDMA), a wireless broadband internet (Wibro) terminal and fixed terminals such as a desktop computer and a smart TV.

An example of the network for sharing information between the present apparatus 100, the CTD device 200, the user terminal 300, and the external server 400 may include a 3rd generation partnership project (3GPP) network, a long term evolution (LTE) network, a 5G network, a world interoperability for microwave access (WiMAX) network, wired/wireless Internet, a local area network (LAN), a wireless local area network (wireless LAN), a wide area network (WAN), a personal area network (PAN), a Bluetooth network, a WiFi network, a near field communication (NFC) network, a satellite broadcasting network, an analog broadcasting network, a digital multimedia broadcasting (DMB) network, and the like, but is not limited thereto.

Figure 2:
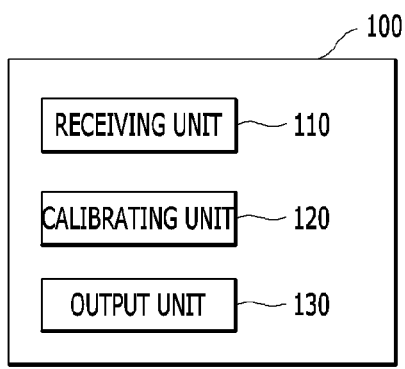
FIG. 2 is a schematic block diagram of a CTD observation information calibrating apparatus according to an exemplary embodiment of the present disclosure.

FIG. 2 is a schematic block diagram of a CTD observation information calibrating apparatus 100 according to an exemplary embodiment of the present disclosure.

Referring to FIG. 2, this apparatus 100 may include a receiving unit 110, a calibrating unit 120, and an output unit 130. The configuration of this apparatus 100 may be further divided into additional configurations or combined with smaller configurations depending on the implementation example of the present disclosure. Further, some configurations may be omitted if necessary and the order of configurations may be changed.

According to the exemplary embodiment of the present disclosure, the receiving unit 110 may receive CTD observation raw information.

According to the exemplary embodiment of the present disclosure, the calibrating unit 120 may calibrate CTD observation raw information.

According to the exemplary embodiment of the present disclosure, the output unit 130 may output the calibrated CTD observation information.

Figure 3:
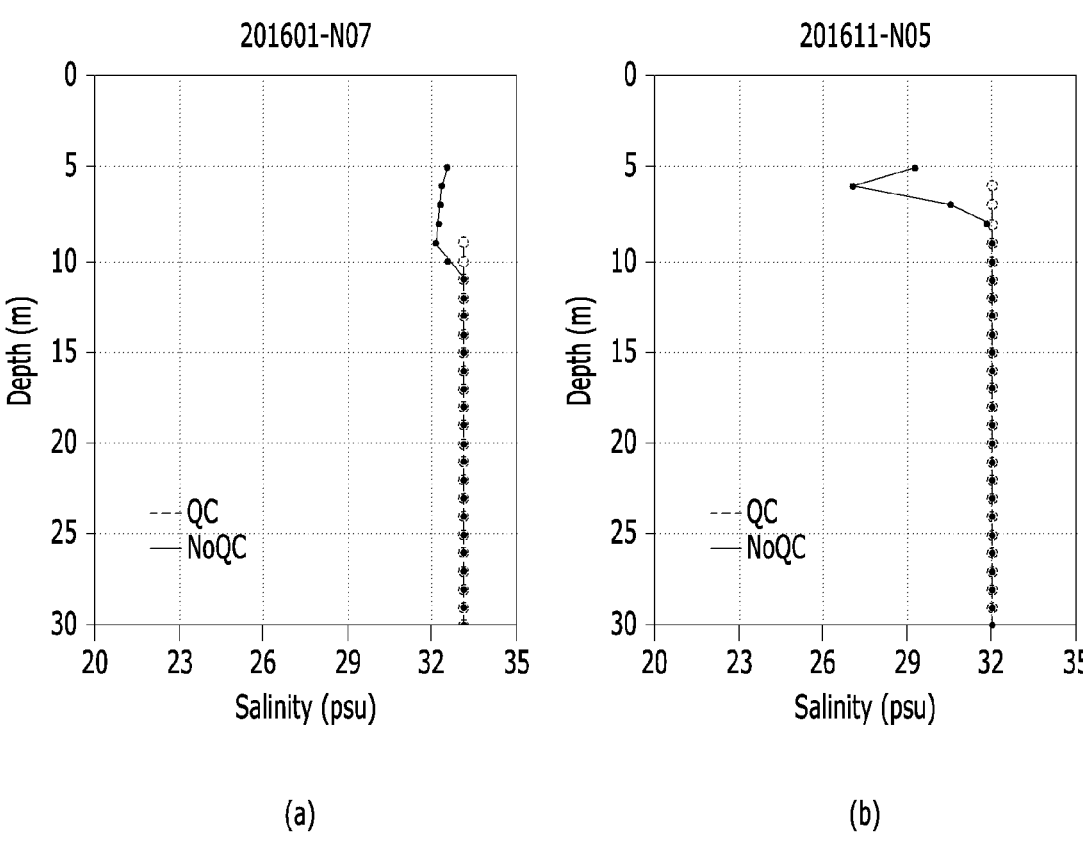
FIG. 3 is a view illustrating an example before and after calibrating CTD observation information on a graph according to an exemplary embodiment of the present disclosure.

FIG. 3 is a view illustrating an example before and after calibrating CTD observation information on a graph according to an exemplary embodiment of the present disclosure.

Referring to FIG. 3, FIG. 3A is a graph illustrating a salinity for every water depth of seawater of one shore region on January 2016 and FIG. 3B is a graph illustrating a salinity for every water depth of seawater of one shore region on November 2016. The normal line indicates a salinity for every water depth included in the CTD observation raw information and the dotted line indicates a salinity for every water depth included in the CTD observation information calibrated by the present apparatus 100. It is confirmed that the CTD observation raw information from which a salinity ratio is not constantly observed is calibrated by this apparatus 100 to have a constant salinity ratio regardless of the depth of water.

According to the exemplary embodiment of the present disclosure, the present apparatus 100 may receive CTD observation raw information.

For example, the present apparatus 100 may receive the CTD observation raw information from the CTD device 200 by the control of the user terminal 300. The CTD observation raw information may refer to observation information about a seawater within a predetermined radius from the CTD device 200 and include at least one of a depth of water, a water temperature, a salinity, an electrical conductivity, a dissolved oxygen, and pH.

As another example, the present apparatus 100 may receive the CTD observation raw information from a plurality of CTD devices 200 by the control of the user terminal 300 by grouping the CTD observation raw information from the plurality of CTD devices 200 which is located with a predetermined threshold interval in a predetermined unit sea region. The present apparatus 100 may receive any one of CTD observation raw information grouped for every unit sea region among all the sea regions to be observed and CTD observation raw information.

According to the exemplary embodiment of the present disclosure, the present apparatus 100 may calibrate CTD observation raw information.

For example, when the present apparatus 100 receives the CTD observation raw information from the CTD device 200, the present apparatus 100 determines whether at least one information of water depth information, water temperature information, salinity information, electrical conductivity information, dissolved oxygen information, and pH information included in the CTD observation raw information needs to be calibrated and allows information which is not necessary to be calibrated to be included in final CTD observation information and calibrates information which is determined to be calibrated and then allows the calibrated CTD observation information to be included in the final CTD observation information.

As another example, when the present apparatus 100 receives the grouped CTD observation raw information from the plurality of CTD devices 200, the present apparatus 100 determines whether it needs to calibrate at least one information group of a water depth information group, a water temperature information group, a salinity information group, an electrical conductivity information group, a dissolved oxygen information group, and a pH information group included in the grouped CTD observation raw information. Thereafter, the present apparatus 100 selects a representative value according to a predetermined criterion from the information group which does not need to be calibrated to be included in the final CTD observation information of the corresponding unit sea region and selects a representative value according to a predetermined criterion from an information group which needs to be calibrated to be calibrated, and then allows the calibrated CTD observation information to be included in the final CTD observation information of the unit sea region.

According to the exemplary embodiment of the present disclosure, the present apparatus 100 may output the calibrated CTD observation information.

For example, the present apparatus 100 allows an interface provided in the user terminal 300 to output the final CTD observation information including the calibrated CTD observation information and may display the calibrated CTD observation information included in the final CTD observation information to be visibly distinguished from the CTD observation raw information (information which is confirmed as final CTD observation information without being calibrated) and write calibrated contents and flag information based on the calibrated contents together with the calibrated CTD observation information included in the final CTD observation information.

As another example, the present apparatus 100 allows an interface provided in the user terminal 300 to output final CTD observation information including calibrated CTD observation information such that the final CTD observation information is output by at least one classification of classification by every unit sea region, classification by every water depth, classification by every water temperature, classification by every salinity, classification by every electrical conductivity, classification by every dissolved oxygen, and classification by every pH, based on the user input. For example, the classification by unit sea region may mean that the corresponding final CTD observation information is classified by unit sea regions. Further, the classification by water depth means that the corresponding final CTD observation information is classified by water depths. Further, the classification by water temperature means that the corresponding final CTD observation information is classified by water temperatures. Further, the classification by salinity means that the corresponding final CTD observation information is classified by water salinity (In this case, in principle, the entire final CTD observation information is classified by one salinity classification and this may allow a user to recognize that when there is a plurality of salinity classifications, a probability of including an error is high). Further, the classification by electrical conductivity means that the corresponding final CTD observation information is classified by electrical conductivities. Further, the classification by dissolved oxygen means that the corresponding final CTD observation information is classified by dissolved oxygens. Further, the classification by pH means that the corresponding final CTD observation information is classified by pHs.

FIG. 4 is a view illustrating an example of a flag information setting screen according to an exemplary embodiment of the present disclosure.

Referring to FIG. 4, the present apparatus 100 may provide an interface which sets a reference for calculating flag information to the user terminal 300 through the user input. Even though in FIG. 4, the flag information calculating reference is set to be displayed as 0 or 1, but it is not limited to a number.

According to an exemplary embodiment of the present disclosure, the present apparatus 100 may write pump flag information to the CTD observation raw information based on a pump state.

For example, the CTD observation raw information may include at least one of a pump operating state of the CTD device 200, an observation starting water depth of a sea region to be observed by the CTD device 200, an observation ending water depth of a sea region to be observed by the CTD device 200, an observation start time, and an observation end time. The CTD observation raw information may include information observed at a frequency of a predetermined threshold frequency. The pump flag information may include a first flag and a second flag. The first flag and the second flag are not equal and may include identified information, respectively. For example, the first flag may be 0 and the second flag may be 1. For example, if the threshold frequency is 24, the pump flag information may be 24 per second.

The present apparatus 100 may write a first flag corresponding to a state in which a power is not input (a pump of the CTD device 200 does not operate) and a second flag corresponding to a state in which a power is input (a pump of the CTD device 200 operates), based on a pump operating state of the CTD device 200.

According to the exemplary embodiment, the present apparatus 100 may derive first valid information from the CTD observation raw information based on the pump flag information.

For example, the present apparatus 100 may derive information corresponding to the second flag from the CTD observation raw information and derive information corresponding to the second flag after a predetermined time, among the derived information corresponding to the second flag, as first valid information.

As another example, the present apparatus 100 may derive information corresponding to the second flag corresponding to a range from the observation starting water depth of the sea region to be observed by the CTD device 200 to the observation ending water depth of the sea region to be observed by the CTD device 200, among the CTD observation raw information, as first valid information.

As another example, the present apparatus 100 may derive information corresponding to the second flag corresponding to a range from the observation start time of the sea region to be observed by the CTD device 200 to the observation end time of the sea region to be observed by the CTD device 200, among the CTD observation raw information, as first valid information.

As another example, the present apparatus 100 may derive information corresponding to a range from a second flag corresponding to an order of a number obtained by multiplying a numerical value of a threshold frequency and a predetermined threshold constant, among the second flag of the CTD observation raw information, to a second frag corresponding to a predetermined order, as first valid information. For example, when the threshold frequency is 24, the predetermined number is 5, and the predetermined order is 1000, after writing a first frag of 0 and a second frag of 1 to the CTD observation raw information based on the pump operating state, the present apparatus 100 may skip information corresponding to the pump frag information which is 0, among the CTD observation raw information and may derive information corresponding to a range from a time when there are 120 pump flag information which is 1 to a time when there are 1000 pump flag information which is 1, as first valid information.

As another example, the present apparatus 100 may increase the threshold constant to be equal to or higher than a predetermined degree when a calibrated ratio of the CTD observation raw information is equal to or higher than a predetermined degree based on the CTD observation raw information and the calibrated CTD observation information.

According to an exemplary embodiment of the present disclosure, in the present apparatus 100, a noise is attenuated from the first valid information to generate second valid information.

As an example, in the present apparatus 100, a noise higher than or equal to a predetermined threshold noise is attenuated from the first valid information to generate second valid information. In contrast, when there is no noise higher than or equal to the threshold noise in the first valid information, the present apparatus 100 may generate first valid information as second valid information.

As another example, the present apparatus 100 may decrease the threshold noise to be lower than a predetermined degree when a calibrated ratio of the CTD observation raw information is equal to or higher than a predetermined degree based on the CTD observation raw information and the calibrated CTD observation information.

According to the exemplary embodiment of the present disclosure, the present apparatus 100 may generate the second valid information based on a predetermined median part of the predetermined information for every water depth included in the first valid information.

As an example, the present apparatus 100 may sort the corresponding first valid information for every water depth information. In order to attenuate the noise, the present apparatus 100 may set a representative value for every water depth by averaging information of median parts excluding an upper threshold ratio and a lower threshold ratio of the first valid information sorted for every water depth and generate information of the median part excluding the upper threshold ratio and the lower threshold ratio of the first valid information from which the representative value for every water depth is set, as second valid information. At this time, when the information of the median parts is averaged to set a representative value for every water depth, it means that values obtained by averaging the information of the median part for every water depth are set as representative values for every water depth.

For example, when the upper threshold ratio and the lower threshold ratio are 25%, respectively, the present apparatus 100 may set a representative value for every water depth by averaging the information of the median part of 50% excluding the upper 25% and the lower 25% of the first valid information sorted for every water depth and generate information of the median part of 50% from which a representative value for every water depth is set, as second valid information.

As another example, the present apparatus 100 may increase the upper threshold ratio and the lower threshold ratio to be equal to or higher than a predetermined degree when a calibrated ratio of the CTD observation raw information is equal to or higher than a predetermined degree based on the CTD observation raw information and the calibrated CTD observation information.

As another example, the present apparatus 100 may write noise flag information to the second valid information based on whether to perform the noise attenuation. The present apparatus 100 may write a third flag to the second valid information on which the noise attenuation is not performed and write a fourth flag to the second valid information on which the noise attenuation is performed. The noise flag information may include a third flag and a fourth flag. The third flag and the fourth flag are not equal to each other, but may include identified information, respectively. For example, the third flag may be 0 and the fourth flag may be 1.

According to the exemplary embodiment of the present disclosure, the present apparatus 100 may determine whether water temperature information and salinity information for every water depth included in the second valid information are present within a predetermined threshold water temperature range and a predetermined threshold salinity range for every water depth, respectively.

As an example, the present apparatus 100 may determine whether the water temperature information for every water depth and the salinity information for every water depth included in the second valid information are present within a predetermined threshold water temperature range for every water depth and the predetermined threshold salinity range for every water depth and perform the determination for every water depth in a predetermined order.

For example, a threshold water temperature range may be −5° C. to 40° C. and a threshold salinity range may be 0 psu to 45 psu.

As another example, the present apparatus 100 may set normal water temperature range information and normal salinity range information received from the external server 400 as a threshold water temperature range and a threshold salinity range.

According to the exemplary embodiment of the present disclosure, the present apparatus 100 inserts a predetermined missing value to water temperature information present out of the threshold water temperature range and salinity information present out of the threshold salinity range to generate third valid information.

As an example, the present apparatus 100 inserts a predetermined missing value to water temperature information for every water depth present out of the predetermined threshold water temperature range for every water depth and salinity information for every water depth present out of the predetermined threshold salinity range for every water depth to generate the third valid information. Insertion may mean substitution.

In contrast, when there are no water temperature information out of the threshold water temperature range and salinity information out of the threshold salinity range in the second valid information, the present apparatus 100 may generate the second valid information as third valid information.

As another example, the present apparatus 100 may decrease the threshold water temperature range and the threshold salinity range to be lower than a predetermined degree when a calibrated ratio of the CTD observation raw information is equal to or higher than a predetermined degree based on the CTD observation raw information and the calibrated CTD observation information.

As another example, the present apparatus 100 may write threshold range flag information to the third valid information based on whether to insert the missing value depending on the determination of the threshold water temperature range and the threshold salinity range. The present apparatus 100 may write a fifth flag to the third valid information into which the missing value is not inserted depending on the determination of the threshold water temperature range and the threshold salinity range and write a sixth flag to the third valid information into which the missing value is inserted depending on the determination of the threshold water temperature range and the threshold salinity range. Threshold range flag information may include a fifth flag and a sixth flag. The fifth flag and the sixth flag are not equal to each other but may include identified information, respectively. For example, the fifth flag may be 0 and the sixth flag may be 1.

According to the exemplary embodiment of the present disclosure, the present apparatus 100 may insert a missing value to information having a difference from information for every water depth adjacent by a predetermined degree which is equal to or larger than a threshold degree based on predetermined information for every adjacent water depth in the third valid information and write spike flag information to generate fourth valid information.

As an example, the spike flag information may include a seventh flag and an eighth flag. The seventh flag and the eighth flag are not equal to each other but may include identified information, respectively. For example, the seventh flag may be 0 and the eighth flag may be 1.

As another example, when the difference between information corresponding to target water depth information and information corresponding to the water depth information adjacent to the target water depth information by a predetermined degree is not equal to or larger than a threshold degree based on the information for every adjacent water depth in the third valid information, the present apparatus 100 may write the seventh flag to the third valid information to generate fourth valid information.

In contrast, when the difference between information corresponding to target water depth information and information corresponding to the water depth information adjacent to the target water depth information by a predetermined degree is equal to or larger than a threshold degree based on the information for every adjacent water depth information in the third valid information, the present apparatus 100 may insert a predetermined missing value to the information with a difference equal to or larger than the threshold degree based on the information for every adjacent water depth corresponding to the target water depth information and write the eighth flat to generate fourth valid information.

As another example, the present apparatus 100 may decrease the threshold degree based on the information for every adjacent water depth to be lower than a predetermined degree when a calibrated ratio of the CTD observation raw information is equal to or higher than a predetermined degree based on the CTD observation raw information and the calibrated CTD observation information.

According to the exemplary embodiment of the present disclosure, the present apparatus 100 may generate fifth valid information by writing consecutive same value flag information to the fourth valid information based on the sameness of the information within a predetermined unit water depth range.

As an example, the consecutive same value flag information may include a ninth flag and a tenth flag. The ninth flag and the tenth flag are not equal to each other, but may include identified information, respectively. For example, the ninth flag may be 0 and the tenth flag may be 1.

As another example, when information corresponding to upper adjacent water depth information and lower adjacent water depth information upwardly and downwardly adjacent to the target water depth information by a predetermined threshold adjacent degree is not equal to the information corresponding to the target water depth information in the fourth valid information, the present apparatus 100 may write the ninth flag to generate fifth valid information.

when information corresponding to upper adjacent water depth information and lower adjacent water depth information upwardly and downwardly adjacent to the target water depth information by a predetermined threshold adjacent degree is equal to the information corresponding to the target water depth information in the fourth valid information, the present apparatus 100 may write the tenth flag to generate fifth valid information and the same position may be written together with the tenth flag to generate the fifth valid information.

As another example, the present apparatus 100 may decrease the threshold adjacent degree to be lower than a predetermined degree when a calibrated ratio of the CTD observation raw information is equal to or higher than a predetermined degree based on the CTD observation raw information and the calibrated CTD observation information.

According to the exemplary embodiment of the present disclosure, the present apparatus 100 may write climatic value flag information to information present out of the predetermined threshold climatic value range in the fifth valid information to generate sixth valid information.

As an example, the climatic value flag information may include an eleventh flag and a twelfth flag. The eleventh flag and the twelfth flag are not equal to each other, but may include identified information, respectively. For example, the eleventh flag may be 0 and the twelfth flag may be 1.

As another example, when there is no information out of the predetermined threshold climatic value range in the fifth valid information, the present apparatus 100 may write the eleventh flag or generate sixth valid information without writing the climatic value flag information.

In contrast, the present apparatus 100 may write the twelfth information to information present out of the threshold climatic value range in the fifth valid information to generate sixth valid information.

As another example, the threshold climatic value range may refer to a range of a predetermined multiple of a standard deviation (+no, n is a positive real number) based on a predetermined threshold climatic value. The threshold climatic value may be information received by the present apparatus 100 from the external server 400.

As another example, the present apparatus 100 may decrease the threshold climatic value range to be lower than a predetermined degree when a calibrated ratio of the CTD observation raw information is equal to or higher than a predetermined degree based on the CTD observation raw information and the calibrated CTD observation information.

According to the exemplary embodiment, the present apparatus 100 may write density inversion flag information to the sixth valid information based on a density difference from an upper water depth within a predetermined range to generate calibrated CTD observation information.

As an example, the inversion flag information may include a thirteenth flag and a fourteenth flag. The thirteenth flag and the fourteenth flag are not equal to each other, but may include identified information, respectively. For example, the thirteenth flag may be 0 and the fourteenth flag may be 1.

As another example, when the difference between density information corresponding to target water depth information and density information corresponding to upper water depth information in a predetermined threshold range is not equal to or larger than a predetermined threshold density in sixth valid information, the present apparatus 100 may write the thirteenth flag to generate calibrated CTD observation information.

In contrast, when the difference between density information corresponding to target water depth information and density information corresponding to upper water depth information in a threshold range is equal to or larger than a threshold density in the sixth valid information, the present apparatus 100 may write the fourteenth flag to density information corresponding to target water depth information to generate calibrated CTD observation information.

As another example, the present apparatus 100 may decrease the threshold density to be lower than a predetermined degree when a calibrated ratio of the CTD observation raw information is equal to or higher than a predetermined degree based on the CTD observation raw information and the calibrated CTD observation information.

According to an exemplary embodiment of the present disclosure, when a specific value does not satisfy a condition, the present apparatus 100 may replace the specific value with a predetermined missing value.

As an example, during a process of writing the first to fourteenth flags, when a target specific value does not satisfy a condition for writing at least one specific flag among the first to fourteenth flags, the present apparatus 100 may replace the specific value with the predetermined missing value.

According to the exemplary embodiment of the present disclosure, the present apparatus 100 may write flag information in CTD observation raw information for every water depth.

As an example, the present apparatus 100 may write the water depth flag information in the CTD observation raw information, the first to sixth valid information, and the calibrated CTD observation information for every water depth information. At this time, when there is an n-th flag (n is an even number) among the fifth to fourteenth flags in the CTD observation raw information, the first to sixth valid information, and the calibrated CTD observation information, the present apparatus 100 may write the n-th flag together with water depth flag information corresponding to the n-th flag.

FIG. 5 is a view illustrating a flag information output screen according to an exemplary embodiment of the present disclosure.

Referring to FIG. 5, the present apparatus 100 may write and output the CTD observation raw information, the calibrated CTD observation information, and flag information (a) together to the interface provided to the user terminal 300. The present apparatus 100 may output the CTD observation raw information, the calibrated CTD observation information, and the flag information together to allow the user to directly determine whether to utilize the information.

According to the exemplary embodiment of the present disclosure, the present apparatus 100 may output flag information corresponding to the calibrated CTD observation information.

As an example, when there is an n-th flag (n is an even number) in the fifth flag to the fourteenth flag in the calibrated CTD observation information, the present apparatus 100 may provide the n-th flag and the water depth flag information corresponding to the n-th flag to the interface provided in the user terminal 300 as a notification.

Hereinafter, an operational flow of the present disclosure will be described in brief based on the above detailed description.

Figure 6:
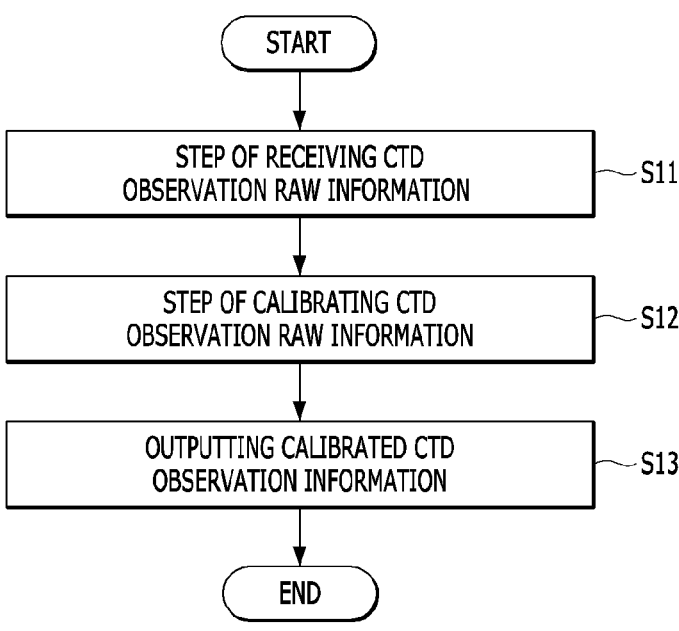
FIG. 6 is an operational flowchart of a control method of a CTD observation information calibrating apparatus according to an exemplary embodiment of the present disclosure.

FIG. 6 is an operational flowchart of a control method of a CTD observation information calibrating apparatus 100 according to an exemplary embodiment of the present disclosure.

Figure 7:
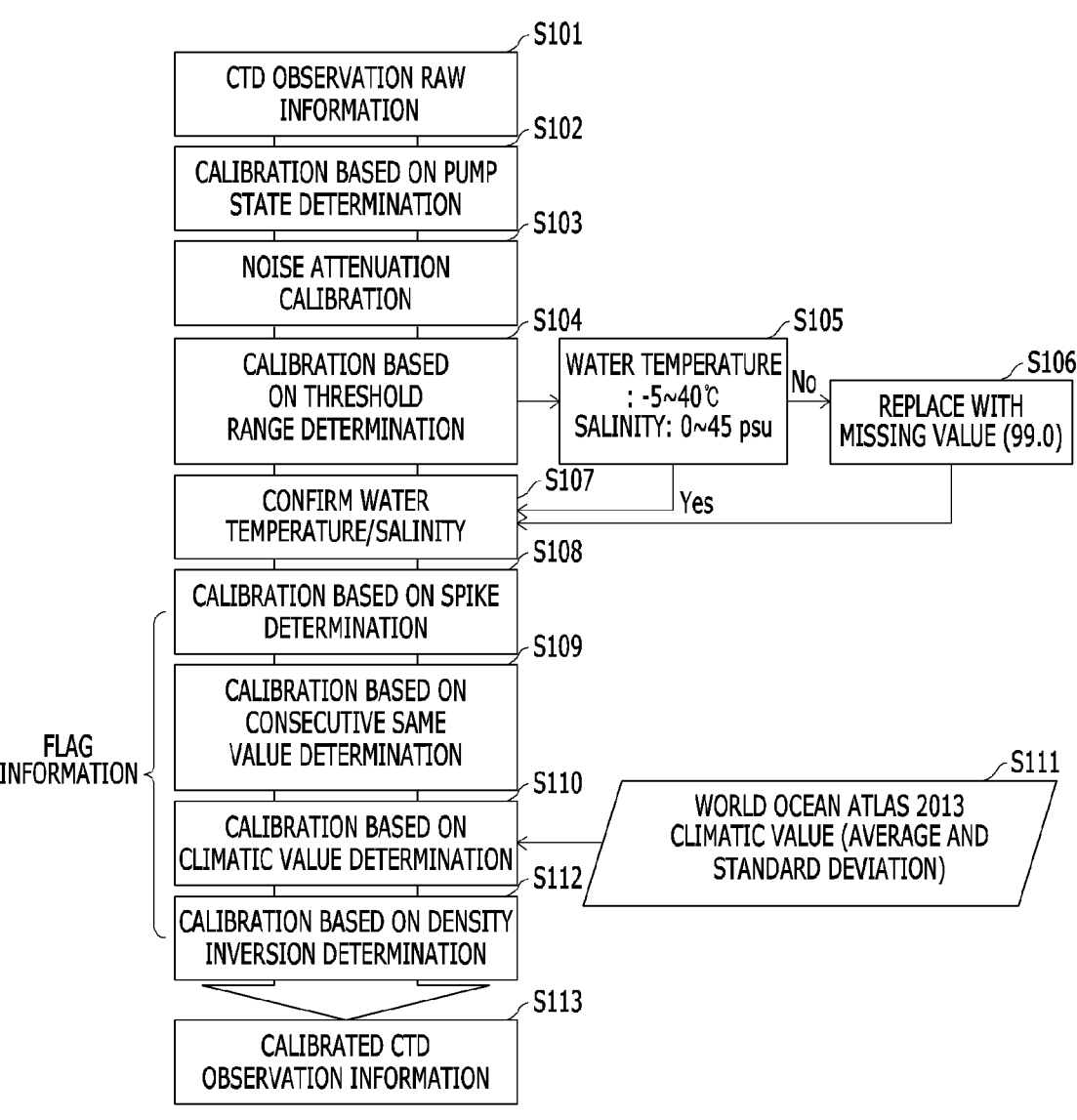
FIG. 7 is an operational flowchart of a control method of a CTD observation information calibrating apparatus according to an exemplary embodiment of the present disclosure.

FIG. 7 is an operational flowchart of a control method of a CTD observation information calibrating apparatus 100 according to an exemplary embodiment of the present disclosure.

A control method of the CTD observation information calibrating apparatus 100 illustrated in FIGS. 6 and 7 may be performed by the present apparatus 100 described above. Therefore, even though some contents are omitted below, the contents which have been described for the present apparatus 100 may be applied to the description for the control method of the CTD observation information calibrating apparatus 100 in the same way.

Referring to FIG. 6, the control method of the CTD observation information calibrating apparatus 100 may include steps S11 to S13.

In step S11, the present apparatus 100 may receive CTD observation raw information.

In step S12, the present apparatus 100 may calibrate CTD observation raw information.

In step S13, the present apparatus 100 may output the calibrated CTD observation information.

Referring to FIG. 7, the control method of the CTD observation information calibrating apparatus 100 may include steps S101 to S113.

In step S101, the present apparatus 100 may receive CTD observation raw information.

Next, in step S102, the present apparatus 100 may calibrate CTD observation raw information based on pump state determination.

Next, in step S103, the present apparatus 100 may perform the noise attenuation calibration on information calibrated in the previous step.

Next, in step S104, the present apparatus 100 may perform a calibration on information calibrated in the previous step based on threshold range determination.

Next, in step S105, the present apparatus 100 may determine whether the water temperature and the salinity included in the information calibrated in step S103 are present within a threshold range of −5° C. to 40° C. and a threshold range of 0 psu to 45 psu, respectively.

Next, in step S106, the present apparatus 100 may replace information out of the threshold range with a missing value which is 99.0 based on the determination result of the previous step.

Next, in step S107, the present apparatus 100 may confirm the water temperature and the salinity based on at least one of information calibrated in step S104, information present within a result threshold range determined in step S105, and information replaced in step S106.

Next, in step S108, the present apparatus 100 may perform a calibration on information confirmed in the previous step based on spike determination.

Next, in step S109, the present apparatus 100 may perform the calibration on information calibrated in the previous step based on consecutive same value determination.

Next, in step S110, the present apparatus 100 may perform the calibration on information calibrated in the previous step based on climatic value determination.

Next, in step S111, the present apparatus 100 may utilize an average and a standard deviation of the world ocean Atlas 2013 climatic values for calibration performed in the previous step as a reference.

Next, in step S112, the present apparatus 100 may perform the calibration on information calibrated in step S110 based on density inversion determination.

Next, in step S113, the present apparatus 100 may output the information calibrated in the previous step as calibrated CTD observation information.

In the above-description, steps S11 to S13 and steps S101 to S113 may be further divided into additional steps or combined as smaller steps depending on an implementation example of the present disclosure. Further, some steps may be omitted as needed and an order between steps may be changed.

The CTD observation information calibrating apparatus 100 according to the exemplary embodiment of the present disclosure may be implemented as a program command which may be executed by various computers to be recorded in a computer readable medium. The computer readable medium may include solely a program command, a data file, and a data structure or a combination thereof. The program command recorded in the medium may be specifically designed or constructed for the present disclosure or known to those skilled in the art of a computer software to be used. Examples of the computer readable recording medium include magnetic media such as a hard disk, a floppy disk, or a magnetic tape, optical media such as a CD-ROM or a DVD, magneto-optical media such as a floptical disk, and a hardware device which is specifically configured to store and execute the program command such as a ROM, a RAM, and a flash memory. Examples of the program command include not only a machine language code which is created by a compiler but also a high level language code which may be executed by a computer using an interpreter. The hardware device may operate as one or more software modules in order to perform the operation of the present disclosure and vice versa.

Further, the above-described CTD observation information calibrating apparatus 100 may also be implemented as a computer program or an application executed by a computer which is stored in a recording medium.

The above-description of the present disclosure is illustrative only and it is understood by those skilled in the art that the present disclosure may be easily modified to another specific type without changing the technical spirit of an essential feature of the present disclosure. Thus, it is to be appreciated that the embodiments described above are intended to be illustrative in every sense, and not restrictive. For example, each component which is described as a singular form may be divided to be implemented and similarly, components which are described as a divided form may be combined to be implemented.

The scope of the present disclosure is represented by the claims to be described below rather than the detailed description, and it is to be interpreted that the meaning and scope of the claims and all the changes or modified forms derived from the equivalents thereof come within the scope of the present disclosure.

What is claimed is:

1. A conductivity temperature depth (CTD) observation information calibrating method, comprising:

receiving CTD observation raw information provided by a CTD device with respect to a region of a body of water;

calibrating the CTD observation raw information, wherein calibrating the CTD observation raw information comprises writing pump flag information to the CTD observation raw information based on a pump state of the CTD device;

outputting calibrated CTD observation information based on calibrating the CTD observation raw information; and outputting, from among the pump flag information written to the CTD observation raw information, flag information corresponding to the calibrated CTD observation information.

2. The CTD observation information calibrating method according to claim 1, wherein writing the pump flag information to the CTD observation raw information is according to a frequency associated with receiving the CTD observation raw information.

3. The CTD observation information calibrating method according to claim 1, wherein in the calibrating, first valid information is derived from the CTD observation raw information based on the pump flag information.

4. The CTD observation information calibrating method according to claim 3, wherein the calibrating includes:

generating second valid information by attenuating noise from the first valid information.

5. The CTD observation information calibrating method according to claim 4, wherein in the generating of second valid information, the second valid information is generated based on a predetermined median part of predetermined information for every water depth included in the first valid information.

6. The CTD observation information calibrating method according to claim 4, wherein in the calibrating, after determining whether water temperature information and salinity information included in the second valid information are present within a predetermined threshold water temperature range and a predetermined threshold salinity range, respectively, a predetermined missing value is inserted into the water temperature information present out of the threshold water temperature range and the salinity information present out of the threshold salinity range to generate third valid information.

7. The CTD observation information calibrating method according to claim 6, wherein in the calibrating, the missing value is inserted into information having a difference from information for every water depth adjacent by a predetermined degree which is equal to or larger than a predetermined degree in the third valid information and spike flag information is written to generate fourth valid information.

8. The CTD observation information calibrating method according to claim 7, wherein in the calibrating, consecutive same value flag information is written in the fourth valid information based on sameness of information within a predetermined unit water depth range to generate fifth valid information.

9. The CTD observation information calibrating method according to claim 8, wherein in the calibrating, climatic value flag information is written in information present out of a predetermined threshold climatic value range of the fifth valid information to generate sixth valid information.

10. The CTD observation information calibrating method according to claim 9, wherein in the calibrating, density inversion flag information is written in the sixth valid information based on density difference from an upper water depth within a predetermined range to generate the calibrated CTD observation information.

11. The CTD observation information calibrating method according to claim 1, wherein in the calibrating, when a specific value does not satisfy a condition, the specific value is replaced with a predetermined missing value.

12. The CTD observation information calibrating method according to claim 1, wherein in the calibrating, the pump flag information is written in the CTD observation raw information for every water depth.

13. A non-transitory computer readable recording medium in which a program allowing a computer to execute the method of claim 1 is recorded.

14. A conductivity temperature depth (CTD) observation information calibrating apparatus, comprising:

a receiving unit configured to receive CTD observation raw information provided by a CTD device with respect to a region of a body of water;

a calibrating unit configured to calibrate the CTD observation raw information, wherein in calibrating the CTD observation raw information, the calibrating unit is configured to write pump flag information to the CTD observation raw information based on a pump state of the CTD device; and an output unit configured to:

output calibrated CTD observation information based on calibrating the CTD observation raw information; and output, from among the pump flag information written to the CTD observation raw information, flag information which corresponds to the calibrated CTD observation information.

* * * * *